(12) United States Patent
Cahoon et al.

(10) Patent No.: US 6,242,256 B1
(45) Date of Patent: Jun. 5, 2001

(54) ORNITHINE BIOSYNTHESIS ENZYMES

(75) Inventors: Edgar B. Cahoon; Rebecca E. Cahoon; William D. Hitz; J. Antoni Rafalski, all of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/347,798

(22) Filed: Jul. 2, 1999

Related U.S. Application Data
(60) Provisional application No. 60/093,209, filed on Jul. 17, 1998.

(51) Int. Cl.[7] ............................... C12N 5/10; C12N 9/02
(52) U.S. Cl. .............................. 435/419; 435/410; 435/6; 435/69.1; 435/189; 435/252.3; 536/23.2
(58) Field of Search ..................... 435/410, 6, 69.1, 435/189, 419, 252.3; 536/23.2

(56) References Cited

PUBLICATIONS

NCBI General Identifier No. 3687224.
NCBI General Identifier No. 4056500.

*Primary Examiner*—Rebecca E. Prouty
*Assistant Examiner*—Richard Hutson

(57) ABSTRACT

This invention relates to an isolated nucleic acid fragment encoding an ornithine biosynthetic enzyme. The invention also relates to the construction of a chimeric gene encoding all or a portion of the ornithine biosynthetic enzyme, in sense or antisense orientation, wherein expression of the chimeric gene results in production of altered levels of the ornithine biosynthetic enzyme in a transformed host cell.

5 Claims, No Drawings

SEQUENCE LISTING

<160> NUMBER OF SEQ ID NOS: 18

<210> SEQ ID NO: 1
<211> LENGTH: 1193
<212> TYPE: DNA
<213> ORGANISM: Helianthus tuberosus

<400> SEQUENCE: 1

```
gcacgaggcg ggtataccgg tgtcgagctt attagattca ttgcatacca tccttacttt      60
ggtatttctc tgatgactgc tgatagaaaa gctagtcaat caattgcttc agtatttcca     120
cacctaatca cacgggattt tccggatttg gttgctgtca aggatgcgga tttttcaagt     180
gtagatgctg ttttttgttg tttgccacat ggcaccactc aggaaattat caaaggtctt     240
ccaactaggt taaaaattgt tgatctttct gcggatttta gattacgaga catcaatgac     300
tacaatgaat ggtacggtca gcctcacaaa gcatcagaat tgcagaaaga ggttgtttat     360
ggtctaacag agatatatag aaacaagatc aaaagtgcac gtcttgttgc aaatcctgga     420
tgttatccta ctactatttt gcttcctctt gttccgttgc tcaaggctag actcattgga     480
ttgcaagata tccttattgt ctcaaactct ggagttagtg gagcaggacg tagtgctaaa     540
gaagcaaatt tatacacgga agtatctgaa gggatatttt cttatggcat cacaaggcat     600
cgccatgtgc ctgaaataga acaagaatta tctgatgctg caaattcaaa agtaaccgtt     660
agctttactc ctaccctaat gccaatgagc cgaggcatgc aatcaactat aaatgtgcaa     720
ttggctccag gagtttccgt tgtggatttg aagcaacacc ttaaggaatt ttatgagaag     780
gaagaatttg tagtggtgtt gccagatgat caagctccac acaccaaata tgttcaaggt     840
```

-continued

```
tccaatggtt gtcatataaa tgtcttcccc gatcgcatcc cagggcgagc aataatcata    900
tccgtcattg ataatcttgt aaagggagct tcgggtcaag ctttacaaaa tcttaacttg    960
atgatgggaa ttccagaaaa caccgggctc agctgcatgc cttttatttcc ttagcccgac  1020
atcctgtttt attgtttttg tcttctttct gtagacttgc gattaggctg ttgtcagatt  1080
tgtttttttt attattgaga aaaggagac aaagttctag ggtttatgtt tacaaacaaa   1140
tgcgcaattt tgaatgtcta cctatttatt ttgaaaaaaa aaaaaaaaaa aaa          1193
```

<210> SEQ ID NO: 2
<211> LENGTH: 337
<212> TYPE: PRT
<213> ORGANISM: Helianthus tuberosus

<400> SEQUENCE: 2

```
Ala Arg Gly Gly Tyr Thr Gly Val Glu Leu Ile Arg Phe Ile Ala Tyr
  1               5                  10                  15

His Pro Tyr Phe Gly Ile Ser Leu Met Thr Ala Asp Arg Lys Ala Ser
                 20                  25                  30

Gln Ser Ile Ala Ser Val Phe Pro His Leu Ile Thr Arg Asp Phe Pro
             35                  40                  45

Asp Leu Val Ala Val Lys Asp Ala Asp Phe Ser Ser Val Asp Ala Val
         50                  55                  60

Phe Cys Cys Leu Pro His Gly Thr Thr Gln Glu Ile Ile Lys Gly Leu
 65                  70                  75                  80

Pro Thr Arg Leu Lys Ile Val Asp Leu Ser Ala Asp Phe Arg Leu Arg
                 85                  90                  95

Asp Ile Asn Asp Tyr Asn Glu Trp Tyr Gly Gln Pro His Lys Ala Ser
            100                 105                 110

Glu Leu Gln Lys Glu Val Val Tyr Gly Leu Thr Glu Ile Tyr Arg Asn
        115                 120                 125

Lys Ile Lys Ser Ala Arg Leu Val Ala Asn Pro Gly Cys Tyr Pro Thr
    130                 135                 140

Thr Ile Leu Leu Pro Leu Val Pro Leu Leu Lys Ala Arg Leu Ile Gly
145                 150                 155                 160

Leu Gln Asp Ile Leu Ile Val Ser Asn Ser Gly Val Ser Gly Ala Gly
                165                 170                 175

Arg Ser Ala Lys Glu Ala Asn Leu Tyr Thr Glu Val Ser Glu Gly Ile
            180                 185                 190

Phe Ser Tyr Gly Ile Thr Arg His Arg His Val Pro Glu Ile Glu Gln
        195                 200                 205

Glu Leu Ser Asp Ala Ala Asn Ser Lys Val Thr Val Ser Phe Thr Pro
    210                 215                 220

Thr Leu Met Pro Met Ser Arg Gly Met Gln Ser Thr Ile Asn Val Gln
225                 230                 235                 240

Leu Ala Pro Gly Val Ser Val Asp Leu Lys Gln His Leu Lys Glu
                245                 250                 255

Phe Tyr Glu Lys Glu Glu Phe Val Val Leu Pro Asp Asp Gln Ala
            260                 265                 270

Pro His Thr Lys Tyr Val Gln Gly Ser Asn Gly Cys His Ile Asn Val
        275                 280                 285

Phe Pro Asp Arg Ile Pro Gly Arg Ala Ile Ile Ser Val Ile Asp
    290                 295                 300

Asn Leu Val Lys Gly Ala Ser Gly Gln Ala Leu Gln Asn Leu Asn Leu
305                 310                 315                 320
```

Met Met Gly Ile Pro Glu Asn Thr Gly Leu Ser Cys Met Pro Leu Phe
             325                 330                 335

Pro

<210> SEQ ID NO: 3
<211> LENGTH: 1411
<212> TYPE: DNA
<213> ORGANISM: Zea mays
<220> FEATURE:
<221> NAME/KEY: unsure
<222> LOCATION: (11)

<400> SEQUENCE: 3

```
gcgccgggac ncgggagaca atggcgttca cgacgctcgg cggctgtggg gcgcaggctt     60
cagtgcggtt ggctccccag aatggaatcc ttggatctaa ttcgaagcca ttcgcgggca    120
tcatactcaa gaaacctcag caggttggat ccctgcccct ccgtgcaagg ggatccattt    180
tttcttcacc acgcaggctt ttctccccta aggcagcagc cctaaatca ggggattcca    240
tacgcattgc agtgctaggg gccagcggtt atactggagc tgagattgtt cggattctag    300
cgaaccaccc tcagtttcat ataaagtga tgactgcaga tagaaaagct ggcgagcaat    360
ttggatcagt atttcctcac ttgataacac aggacctgcc gagactggtc gcaataaaag    420
acgctgactt ttcagatgtt gatgctgttt tttgctgctt gccacatggt acaacccagg    480
aaattatcaa aagcttaccc cgacacttaa agattgttga tctctcagcg gacttccgac    540
tacgcgacat caatgagtat gctgagtggt atggacattc ccacagggca cgggaacttc    600
aggggggaagc tgtgtatggt ttgaccgaac ttaaacgaga tgacataaga aatgcacgcc    660
tggtagcaaa tccagggtgt tatcccacat ctattcaact tccgctcgtt cctttggtaa    720
aggcaaaact gatcaagcta accaacatta ttattgatgc aaaatctgga gtcagtggtg    780
caggacgtgg ggctaaggaa gcaaatcttt acactgaaat cgctgagggt atccatgctt    840
atgggataac aagccatcgg catgtgcctg agattgagca aggacttaca gatgctgctg    900
aatcaaaagt tactatcagc tttactccac atttgatgtg tatgaaacgt gggatgcaat    960
ctactgtgta tgttgaattg gcatctggag tgactcccag ggatttgtat gaacacctaa   1020
agtctactta cgagaatgaa gaatttgtca agctgttaca tggtagcaat gttccttgca   1080
caagccatgt tgtgggatca aattactgct tcatgaatgt ctatgaggat agaataccctg   1140
gaagggccat catcatctct gtcatagata atcttgtgaa gggagcatct ggtcaggctt   1200
tgcaaaatct taatctgatg atgggactgc ctgagaatat ggggctgcaa taccagcccc   1260
tgttcccttg atcttttgtg tcattatcta ttattacatt atttaggagt ccagaaacca   1320
aattatcatt actgtcaaga ggtggcaagg agcctgacat cagaattcag tcaagtcgaa   1380
gttagacagt tagtgtagct tggtctgtgt t                                  1411
```

<210> SEQ ID NO: 4
<211> LENGTH: 416
<212> TYPE: PRT
<213> ORGANISM: Zea mays

<400> SEQUENCE: 4

Met Ala Phe Thr Thr Leu Gly Gly Cys Gly Ala Gln Ala Ser Val Arg
 1               5                  10                  15

Leu Ala Pro Gln Asn Gly Ile Leu Gly Ser Asn Ser Lys Pro Phe Ala
            20                  25                  30

-continued

```
Gly Ile Ile Leu Lys Lys Pro Gln Gln Val Gly Ser Leu Pro Leu Arg
             35                  40                  45

Ala Arg Gly Ser Ile Phe Ser Ser Pro Arg Arg Leu Phe Ser Pro Lys
 50                  55                  60

Ala Ala Ala Pro Lys Ser Gly Asp Ser Ile Arg Ile Ala Val Leu Gly
 65                  70                  75                  80

Ala Ser Gly Tyr Thr Gly Ala Glu Ile Val Arg Ile Leu Ala Asn His
                 85                  90                  95

Pro Gln Phe His Ile Lys Val Met Thr Ala Asp Arg Lys Ala Gly Glu
                100                 105                 110

Gln Phe Gly Ser Val Phe Pro His Leu Ile Thr Gln Asp Leu Pro Arg
            115                 120                 125

Leu Val Ala Ile Lys Asp Ala Asp Phe Ser Asp Val Asp Ala Val Phe
130                 135                 140

Cys Cys Leu Pro His Gly Thr Thr Gln Glu Ile Ile Lys Ser Leu Pro
145                 150                 155                 160

Arg His Leu Lys Ile Val Asp Leu Ser Ala Asp Phe Arg Leu Arg Asp
                165                 170                 175

Ile Asn Glu Tyr Ala Glu Trp Tyr Gly His Ser His Arg Ala Arg Glu
            180                 185                 190

Leu Gln Gly Glu Ala Val Tyr Gly Leu Thr Glu Leu Lys Arg Asp Asp
        195                 200                 205

Ile Arg Asn Ala Arg Leu Val Ala Asn Pro Gly Cys Tyr Pro Thr Ser
210                 215                 220

Ile Gln Leu Pro Leu Val Pro Leu Val Lys Ala Lys Leu Ile Lys Leu
225                 230                 235                 240

Thr Asn Ile Ile Ile Asp Ala Lys Ser Gly Val Ser Gly Ala Gly Arg
                245                 250                 255

Gly Ala Lys Glu Ala Asn Leu Tyr Thr Glu Ile Ala Glu Gly Ile His
            260                 265                 270

Ala Tyr Gly Ile Thr Ser His Arg His Val Pro Glu Ile Glu Gln Gly
        275                 280                 285

Leu Thr Asp Ala Ala Glu Ser Lys Val Thr Ile Ser Phe Thr Pro His
    290                 295                 300

Leu Met Cys Met Lys Arg Gly Met Gln Ser Thr Val Tyr Val Glu Leu
305                 310                 315                 320

Ala Ser Gly Val Thr Pro Arg Asp Leu Tyr Glu His Leu Lys Ser Thr
                325                 330                 335

Tyr Glu Asn Glu Glu Phe Val Lys Leu Leu His Gly Ser Asn Val Pro
            340                 345                 350

Cys Thr Ser His Val Val Gly Ser Asn Tyr Cys Phe Met Asn Val Tyr
        355                 360                 365

Glu Asp Arg Ile Pro Gly Arg Ala Ile Ile Ser Val Ile Asp Asn
    370                 375                 380

Leu Val Lys Gly Ala Ser Gly Gln Ala Leu Gln Asn Leu Asn Leu Met
385                 390                 395                 400

Met Gly Leu Pro Glu Asn Met Gly Leu Gln Tyr Gln Pro Leu Phe Pro
                405                 410                 415
```

<210> SEQ ID NO: 5
<211> LENGTH: 380
<212> TYPE: DNA
<213> ORGANISM: Oryza sativa

<400> SEQUENCE: 5

```
aggatggagt ctttggatct aatctgaagc aatgcggtgg tttcatgctc aaaacaaccc      60
ctaaggttgg atcctcttca gtccgtgtga gggcatctgt tgcttcttca ccgcagaaac     120
agcactctcc caagacatca ggagttaaat caggggagga ggtgcgcatt gcggttctag     180
gtgccagcgg ttatactgga gctgagattg tcaggcttct agcaaaccat cctcaatttc     240
gtatcaaagt gatgactgca gatagaaaag ctggcgaaca gtttggatct gtatttcctc     300
acttaataac acaggacctg ccaaatttag ttgcaagtaa agatgcaga ttttcaaat      360 gtgggatgca gttttttgtt                                                 380
```

<210> SEQ ID NO: 6
<211> LENGTH: 117
<212> TYPE: PRT
<213> ORGANISM: Oryza sativa

<400> SEQUENCE: 6

```
Asp Gly Val Phe Gly Ser Asn Leu Lys Gln Cys Gly Gly Phe Met Leu
 1               5                  10                  15

Lys Thr Thr Pro Lys Val Gly Ser Ser Val Arg Val Arg Ala Ser
             20                  25                  30

Val Ala Ser Ser Pro Gln Lys Gln His Ser Pro Lys Thr Ser Gly Val
         35                  40                  45

Lys Ser Gly Glu Glu Val Arg Ile Ala Val Leu Gly Ala Ser Gly Tyr
     50                  55                  60

Thr Gly Ala Glu Ile Val Arg Leu Leu Ala Asn His Pro Gln Phe Arg
 65                  70                  75                  80

Ile Lys Val Met Thr Ala Asp Arg Lys Ala Gly Glu Gln Phe Gly Ser
                 85                  90                  95

Val Phe Pro His Leu Ile Thr Gln Asp Leu Pro Asn Leu Val Ala Ser
            100                 105                 110

Lys Arg Cys Arg Phe
        115
```

<210> SEQ ID NO: 7
<211> LENGTH: 1713
<212> TYPE: DNA
<213> ORGANISM: Glycine max

<400> SEQUENCE: 7

```
gcacgagatc agttccgtcg tgagacactg tcataacata agagtcgtgg acgcggttgg      60
ctgttgctgt ctacggttcc aacttccaag ttacaagctt cacccatttt ataaaagtta     120
cggttcggtt ccgctgcatt cgtgctttct agcaacacaa aatgagcgcc atctctttca     180
gttccaccca tttgcacagt tggaaaaatc caaggggtt tggaaaggtg agaaagcaac     240
gagatgggaa gctacttgtc aagtgttcca gcaagagtgg gaacccaact tcattgcaaa     300
atggggttcg tgttggtgtt cttggagcta gtggctacac tggttctgag gttatgcgat     360
tcttggctaa tcatccacag tttgggattg cactgatgac tgctgatagg aaagctgggc     420
agccaatctc ttctgtattc ccacatttga gcactcggga cttgccagat tgattgcaa     480 taaaggatgc aaacttttct gatgtggatg ctgtattctg ttgtttgcct catgaactaa     540
ctcaggaaat tattaaaggc ctaccaaagc acttgaagat tgttgatctt tctgcagatt     600
ttcgtctaaa agatctttct gagtatgaag agtggtatgg tcagccgcat agagcaccag     660
atttgcagaa agaagctata tatggattaa cagaggtttt aagggaggaa ataaagaatg     720
```

```
cacgtctagt tgctaatcct ggttgttatc caacttctgt tcaacttcct cttgtcccat    780
tgataaaggc tagtcttatt gagcttaaaa atattatcat tgatgctaaa tctggtgtga    840
gtggagcagg gcgcagtgcc aaagaaaatt tattgttcac tgaagtaact gaaggtctca    900
attcttatgg tgttacccta catcgccatg ttcctgaaat tgagcaggga cttgctgatg    960
cttcaggttc aaaagtaact gttagtttta caccacatct aattccaatg agccgtggta   1020
tgcaatcaac tatttatgtg gaaatggctc caggagtgag aattgaggac ctgtaccagc   1080
aactgaagct ctcatatgag aatgaagaat tgttttttgt gttggaaaat ggagtcattc   1140
ctcgaactca cagcgttaaa gggactaatt actgtttaat caatgttttt ccagaccgaa   1200
ttcctggaag agcaatcatt atatctgtta ttgataatct agtgaaggga gcttcaggtc   1260
aagctttaca aaaccttaat ttgttaatgg gatttccaga aaatttggga cttcattacc   1320
tgcctctttt tccatagagt agttgtcttg tccaactaga gctccaattc tgcagtcaca   1380
gttccaccaa aatacttgat ggagcagagg aaatattttc aagttatgta ttttcgttct   1440
ctagattgta atgtgagatt cttcaagaat ttagaaggga attgattatg gcattggcag   1500
ggatactata gcaatttctg tcttttttgt cctttgtttt gatctgtaat gttagaaatc   1560
actgaaggtg gtggcgtgta gttttccaag tttgggtttt ggtttatttg taatgccaat   1620
attttagtgg actatgaaat caccatctca agttttttgag attttttgttt caatttgact   1680
tactgcctgt tgattttaa aaaaaaaaaa aaa                                  1713
```

<210> SEQ ID NO: 8
<211> LENGTH: 391
<212> TYPE: PRT
<213> ORGANISM: Glycine max

<400> SEQUENCE: 8

```
Met Ser Ala Ile Ser Phe Ser Ser Thr His Leu His Ser Trp Lys Asn
  1               5                  10                  15

Pro Lys Gly Phe Gly Lys Val Arg Lys Gln Arg Asp Gly Lys Leu Leu
                 20                  25                  30

Val Lys Cys Ser Ser Lys Ser Gly Asn Pro Thr Ser Leu Gln Asn Gly
             35                  40                  45

Val Arg Val Gly Val Leu Gly Ala Ser Gly Tyr Thr Gly Ser Glu Val
         50                  55                  60

Met Arg Phe Leu Ala Asn His Pro Gln Phe Gly Ile Ala Leu Met Thr
 65                  70                  75                  80

Ala Asp Arg Lys Ala Gly Gln Pro Ile Ser Ser Val Phe Pro His Leu
                 85                  90                  95

Ser Thr Arg Asp Leu Pro Asp Leu Ile Ala Ile Lys Asp Ala Asn Phe
            100                 105                 110

Ser Asp Val Asp Ala Val Phe Cys Cys Leu Pro His Gly Thr Thr Gln
        115                 120                 125

Glu Ile Ile Lys Gly Leu Pro Lys His Leu Lys Ile Val Asp Leu Ser
    130                 135                 140

Ala Asp Phe Arg Leu Lys Asp Leu Ser Glu Tyr Glu Trp Tyr Gly
145                 150                 155                 160

Gln Pro His Arg Ala Pro Asp Leu Gln Lys Glu Ala Ile Tyr Gly Leu
                165                 170                 175

Thr Glu Val Leu Arg Glu Glu Ile Lys Asn Ala Arg Leu Val Ala Asn
            180                 185                 190

Pro Gly Cys Tyr Pro Thr Ser Val Gln Leu Pro Leu Val Pro Leu Ile
```

```
                195                 200                     205
Lys Ala Ser Leu Ile Glu Leu Lys Asn Ile Ile Asp Ala Lys Ser
    210                 215                 220
Gly Val Ser Gly Ala Gly Arg Ser Ala Lys Glu Asn Leu Leu Phe Thr
225                 230                 235                 240
Glu Val Thr Glu Gly Leu Asn Ser Tyr Gly Val Thr Leu His Arg His
                245                 250                 255
Val Pro Glu Ile Glu Gln Gly Leu Ala Asp Ala Ser Gly Ser Lys Val
                260                 265                 270
Thr Val Ser Phe Thr Pro His Leu Ile Pro Met Ser Arg Gly Met Gln
                275                 280                 285
Ser Thr Ile Tyr Val Glu Met Ala Pro Gly Val Arg Ile Glu Asp Leu
            290                 295                 300
Tyr Gln Gln Leu Lys Leu Ser Tyr Glu Asn Glu Phe Val Phe Val
305                 310                 315                 320
Leu Glu Asn Gly Val Ile Pro Arg Thr His Ser Val Lys Gly Thr Asn
                325                 330                 335
Tyr Cys Leu Ile Asn Val Phe Pro Asp Arg Ile Pro Gly Arg Ala Ile
                340                 345                 350
Ile Ile Ser Val Ile Asp Asn Leu Val Lys Gly Ala Ser Gly Gln Ala
            355                 360                 365
Leu Gln Asn Leu Asn Leu Leu Met Gly Phe Pro Glu Asn Leu Gly Leu
        370                 375                 380
His Tyr Leu Pro Leu Phe Pro
385                 390

<210> SEQ ID NO: 9
<211> LENGTH: 1654
<212> TYPE: DNA
<213> ORGANISM: Triticum aestivum

<400> SEQUENCE: 9
ccgtgccgaa ttcggcacga gtcactccga tcaatctcga tttgccagcc ctccgcgacg     60
ccggcaggtc gctgttgagc ctgactactc cccgtagcgg acatgggatc gacggcgctc    120
ggtggtgcgg ctccggcgcg cgccggattg ccccccaaga gtggagtcct tggatctact    180
ttcaagccat gtggtggttt caagctcaaa acaactacta aggttggacg ctcttcagtt    240
tgtgtgaggg tatccattgc ttcttcacca caaaaacagt actctcctaa gacatcagca    300
gttaaatcag gggaggaagt gcgcattgcg gtgctaggag ccagcggtta taccggggct    360
gagattgttc ggcttctagc aaaccaccct cagttccgta tcacagtgat gaccgcagac    420
agaaaagctg gtgaacagtt tggatctgta tttcctcact tgataacaca agacctgcca    480
aatttagttg cgattaaaga tgcagatttt tcagatgttg atgctgtttt ttgttgcttg    540
ccacatggaa caacacagga aattattaaa ggcttacccc aacaactgaa gattgttgat    600
ctctctgcgg atttccgatt gcgtaacatc aatgagtctg ctgagtggta tggccatgct    660
cataggcac cagaacttca ggaagaggct gtttatggtt tgacggaggt tcttcgagat    720
gaaataagaa atgcacggct tgttgccaac ccgggatgtt atcccacgtc tattcagctc    780
cctcttgttc ctctaataaa ggcaaaactg atcaagctga gcaatataat aattgatgca    840
aaatctgggg ttaccggggc aggacgtgga gctaaggaag caaatctgta caccgagata    900
gctgaaggca ttcatgctta tggaataaaa ggccaccgtc atgttcctga ggttgaacaa    960
ggattgtcag aggctgctga atccaaagtt actatcagct tcactccaaa tcttatctgc   1020
```

-continued

```
atgaaacgtg ggatgcaatc tactatgttt gttgaaatgg cacctggagt gactgtcagt    1080
gatttgtatc agcatctcaa gtctacttat gagggtgaag aatttgtcaa gctgttaaat    1140
ggcagcaatg ttcctcacac acgccatgtt gttggatcaa attactgctt catgaatgtc    1200
ttcgaggaca gaattcctgg aagggcaatc atcatctctg tcatagacaa tcttgtaaag    1260
ggagcatctg gccaggccgt gcagaacctc aatctgatga tgggactgcc tgagaacatg    1320
gggctgcaat atcagcccct atttccttga tatgttgtgc ctttgttgtg ctctttctcg    1380
atgatgcttt ggagttaagc acccatctct gttttccgtt gagaagcaaa gagctgaatg    1440
tcggagtgta accaaactcg ctcaacagca aaacttggtt tgtgctggtg tagtatttag    1500
agaggagcaa caattagcag ttgaataaga gtatgaactg agtggcttgg tgtaatgaaa    1560
gtccaaaggc tattatatcc tacagtggat tgttgtcatg agatcaataa agcagtgtaa    1620
aacccgattc agagacaaaa aaaaaaaaaa aaaa                                1654
```

<210> SEQ ID NO: 10
<211> LENGTH: 415
<212> TYPE: PRT
<213> ORGANISM: Triticum aestivum

<400> SEQUENCE: 10

```
Met Gly Ser Thr Ala Leu Gly Gly Ala Ala Pro Ala Arg Ala Gly Leu
 1               5                  10                  15

Ala Pro Lys Ser Gly Val Leu Gly Ser Thr Phe Lys Pro Cys Gly Gly
            20                  25                  30

Phe Lys Leu Lys Thr Thr Thr Lys Val Gly Arg Ser Ser Val Cys Val
        35                  40                  45

Arg Val Ser Ile Ala Ser Ser Pro Gln Lys Gln Tyr Ser Pro Lys Thr
    50                  55                  60

Ser Ala Val Lys Ser Gly Glu Glu Val Arg Ile Ala Val Leu Gly Ala
65                  70                  75                  80

Ser Gly Tyr Thr Gly Ala Glu Ile Val Arg Leu Leu Ala Asn His Pro
                85                  90                  95

Gln Phe Arg Ile Thr Val Met Thr Ala Asp Arg Lys Ala Gly Glu Gln
            100                 105                 110

Phe Gly Ser Val Phe Pro His Leu Ile Thr Gln Asp Leu Pro Asn Leu
        115                 120                 125

Val Ala Ile Lys Asp Ala Asp Phe Ser Asp Val Asp Ala Val Phe Cys
    130                 135                 140

Cys Leu Pro His Gly Thr Thr Gln Glu Ile Ile Lys Gly Leu Pro Gln
145                 150                 155                 160

Gln Leu Lys Ile Val Asp Leu Ser Ala Asp Phe Arg Leu Arg Asn Ile
                165                 170                 175

Asn Glu Ser Ala Glu Trp Tyr Gly His Ala His Arg Ala Pro Glu Leu
            180                 185                 190

Gln Glu Glu Ala Val Tyr Gly Leu Thr Glu Val Leu Arg Asp Glu Ile
        195                 200                 205

Arg Asn Ala Arg Leu Val Ala Asn Pro Gly Cys Tyr Pro Thr Ser Ile
    210                 215                 220

Gln Leu Pro Leu Val Pro Leu Ile Lys Ala Lys Leu Ile Lys Leu Ser
225                 230                 235                 240

Asn Ile Ile Ile Asp Ala Lys Ser Gly Val Thr Gly Ala Gly Arg Gly
                245                 250                 255
```

-continued

```
Ala Lys Glu Ala Asn Leu Tyr Thr Glu Ile Ala Glu Gly Ile His Ala
            260                 265                 270

Tyr Gly Ile Lys Gly His Arg His Val Pro Glu Val Glu Gln Gly Leu
        275                 280                 285

Ser Glu Ala Ala Glu Ser Lys Val Thr Ile Ser Phe Thr Pro Asn Leu
    290                 295                 300

Ile Cys Met Lys Arg Gly Met Gln Ser Thr Met Phe Val Glu Met Ala
305                 310                 315                 320

Pro Gly Val Thr Val Ser Asp Leu Tyr Gln His Leu Lys Ser Thr Tyr
                325                 330                 335

Glu Gly Glu Glu Phe Val Lys Leu Leu Asn Gly Ser Asn Val Pro His
            340                 345                 350

Thr Arg His Val Val Gly Ser Asn Tyr Cys Phe Met Asn Val Phe Glu
        355                 360                 365

Asp Arg Ile Pro Gly Arg Ala Ile Ile Ile Ser Val Ile Asp Asn Leu
    370                 375                 380

Val Lys Gly Ala Ser Gly Gln Ala Val Gln Asn Leu Asn Leu Met Met
385                 390                 395                 400

Gly Leu Pro Glu Asn Met Gly Leu Gln Tyr Gln Pro Leu Phe Pro
                405                 410                 415
```

<210> SEQ ID NO: 11
<211> LENGTH: 1334
<212> TYPE: DNA
<213> ORGANISM: Zea mays
<220> FEATURE:
<221> NAME/KEY: unsure
<222> LOCATION: (1208)
<220> FEATURE:
<221> NAME/KEY: unsure
<222> LOCATION: (1210)
<220> FEATURE:
<221> NAME/KEY: unsure
<222> LOCATION: (1212)
<220> FEATURE:
<221> NAME/KEY: unsure
<222> LOCATION: (1220)
<220> FEATURE:
<221> NAME/KEY: unsure
<222> LOCATION: (1226)
<220> FEATURE:
<221> NAME/KEY: unsure
<222> LOCATION: (1235)
<220> FEATURE:
<221> NAME/KEY: unsure
<222> LOCATION: (1237)
<220> FEATURE:
<221> NAME/KEY: unsure
<222> LOCATION: (1288)
<220> FEATURE:
<221> NAME/KEY: unsure
<222> LOCATION: (1314)

<400> SEQUENCE: 11

```
ctactgacac agtgacacgc accaatgccc aacccggcgg ccggcctcga acgataacac      60
gccggcccgc ctcgccacgc tcccaccctc ctgcctccgc gcgccacgac cagccgcccc     120
agcagcagat gtcgccccg tccgtcctgc tcctccactc ccgcatcccg cttcagcccc      180
gccccttcag gatgaactcc cgggcagctc cgagcagggt cgtcgtctgc tccgtcgcgt     240
ctaccgaggg gttcatctcc gcagcgccga tcctcctccc cgagggccct tggaaacagg     300
tggaaggcgg cgtcactgcc gcgaaggggt tcaaggcggc gggtatctac agtgggttgc     360
gtgccaaagg cgagaagcct gacttggcac tggtcgcctg cgacgtcgac gccactgtag     420
```

-continued

```
caggagcatt tacaacaaac gtcgtagccg ccgcacctgt tttgtattgc aagcatgtcc    480
ttagtacatc gaaaacaggt cgtgctgtgt taattaatgc tggacaagca aatgctgcaa    540
ctggtgatct tggctatcag gatgcagtgg atagtgcaga tgctgttgcc aagcttctca    600
atgtaagcac agataacata ctgattcagt ctactggtgt cattggtcaa aggataaaga    660
aggaggcact tttaaattca ctacctagac ttgtgggctc actgtcttct tcagttcagg    720
gtgcgaattc tgctgctgtg gccattacaa ctacagacct tgttagcaag agyattgctg    780
tccagactga gattggagga gtggctatta gaataggtgg gatggctaaa ggttctggaa    840
tgattcaccc aaatatggca acaatgcttg gtgttttgac cacagatgct caagtcagca    900
gtgatgtctg gagagaaatg atccggatgt cagtgagtag aagtttcaac caaattacag    960
tggatggtga tactagtacc aatgactgtg ktattgctat ggcaagtggg ttgtctggtt   1020
tatctggaat tcaaagtctt gatagcattg aggctcaaca gttccaagca tgcctagatg   1080
cagtaatgca aagtcttgca aaatccatag catgggatgt gagggtgcc acatgcctat    1140 tggaggttac tgtaagtggc gccaacaacg aggcagaagc tgctaaaaat ggcccgtttc   1200
attagccncn tncctccttn gggttnaaag ccgcngntat ttggggagga acccccaatt   1260 gggggggacga attggcttgg ccccattngg gttattccag gcattccatt ttgncgccaa   1320
accgcctgga aatt                                                     1334
```

<210> SEQ ID NO: 12
<211> LENGTH: 359
<212> TYPE: PRT
<213> ORGANISM: Zea mays
<220> FEATURE:
<221> NAME/KEY: UNSURE
<222> LOCATION: (288)

<400> SEQUENCE: 12

```
Met Ser Pro Pro Ser Val Leu Leu His Ser Arg Ile Pro Leu Gln
 1               5                  10                  15

Pro Arg Pro Phe Arg Met Asn Ser Arg Ala Ala Pro Ser Arg Val Val
                20                  25                  30

Val Cys Ser Val Ala Ser Thr Glu Gly Phe Ile Ser Ala Ala Pro Ile
            35                  40                  45

Leu Leu Pro Glu Gly Pro Trp Lys Gln Val Glu Gly Val Thr Ala
    50                  55                  60

Ala Lys Gly Phe Lys Ala Ala Gly Ile Tyr Ser Gly Leu Arg Ala Lys
65                  70                  75                  80

Gly Glu Lys Pro Asp Leu Ala Leu Val Ala Cys Asp Val Asp Ala Thr
                85                  90                  95

Val Ala Gly Ala Phe Thr Thr Asn Val Ala Ala Pro Val Leu
            100                 105                 110

Tyr Cys Lys His Val Leu Ser Thr Ser Lys Thr Gly Arg Ala Val Leu
        115                 120                 125

Ile Asn Ala Gly Gln Ala Asn Ala Ala Thr Gly Asp Leu Gly Tyr Gln
    130                 135                 140

Asp Ala Val Asp Ser Ala Asp Ala Val Ala Lys Leu Leu Asn Val Ser
145                 150                 155                 160

Thr Asp Asn Ile Leu Ile Gln Ser Thr Gly Val Ile Gly Gln Arg Ile
                165                 170                 175

Lys Lys Glu Ala Leu Leu Asn Ser Leu Pro Arg Leu Val Gly Ser Leu
            180                 185                 190
```

```
Ser Ser Ser Val Gln Gly Ala Asn Ser Ala Ala Val Ala Ile Thr Thr
        195                 200                 205

Thr Asp Leu Val Ser Lys Ser Ile Ala Val Gln Thr Glu Ile Gly Gly
    210                 215                 220

Val Ala Ile Arg Ile Gly Gly Met Ala Lys Gly Ser Gly Met Ile His
225                 230                 235                 240

Pro Asn Met Ala Thr Met Leu Gly Val Leu Thr Thr Asp Ala Gln Val
                245                 250                 255

Ser Ser Asp Val Trp Arg Glu Met Ile Arg Met Ser Val Ser Arg Ser
            260                 265                 270

Phe Asn Gln Ile Thr Val Asp Gly Asp Thr Ser Thr Asn Asp Cys Xaa
        275                 280                 285

Ile Ala Met Ala Ser Gly Leu Ser Gly Leu Ser Gly Ile Gln Ser Leu
    290                 295                 300

Asp Ser Ile Glu Ala Gln Gln Phe Gln Ala Cys Leu Asp Ala Val Met
305                 310                 315                 320

Gln Ser Leu Ala Lys Ser Ile Ala Trp Asp Gly Glu Gly Ala Thr Cys
                325                 330                 335

Leu Leu Glu Val Thr Val Ser Gly Ala Asn Asn Glu Ala Glu Ala Ala
            340                 345                 350

Lys Ala Ala Lys Ala Ala Lys
            355
```

<210> SEQ ID NO: 13
<211> LENGTH: 460
<212> TYPE: DNA
<213> ORGANISM: Glycine max
<220> FEATURE:
<221> NAME/KEY: unsure
<222> LOCATION: (442)

<400> SEQUENCE: 13

```
aaggcgttta attctcccct acgcaatttg aggatccgtg ccgtttcaac caaagagaat    60
cacataccag ctgctccaat ttttctcccc gaaggacctt ggaaccagat tccaggtgga   120
gttactgctg ccgagggatt caaagctgcg ggaatgtacg gaggtttacg tgccaaagga   180
gaaaagccta atctcgcgct tgtcacgtgc gatgttgatg cagtatctgc aggatcgttt   240
acaacaaatg tggttgcggc tgcaccggtg ttatactgca aaaggacgtt ggatatttcc   300
aacactgcac gtgctgtgtt aactaatgca ggtcaagcaa atgcagcgac gggcaaagaa   360
ggttaccaag acatgatag aatgtgtgga aagccttgct aagctatttg aaagtgaagc   420
caagaaagaa gtattaattg antccactgg gtgtaattgg                         460
```

<210> SEQ ID NO: 14
<211> LENGTH: 443
<212> TYPE: PRT
<213> ORGANISM: Glycine max

<400> SEQUENCE: 14

```
Lys Ala Phe Asn Ser Pro Leu Arg Asn Leu Arg Ile Arg Ala Val Ser
  1               5                  10                  15

Thr Lys Glu Asn His Ile Pro Ala Pro Ile Phe Leu Pro Glu Gly
             20                  25                  30

Pro Trp Asn Gln Ile Pro Gly Val Thr Ala Ala Glu Gly Phe Lys
         35                  40                  45

Ala Ala Gly Met Tyr Gly Gly Leu Arg Ala Lys Gly Glu Lys Pro Asp
    50                  55                  60
```

-continued

```
Leu Ala Leu Val Thr Cys Asp Val Asp Ala Val Ser Ala Gly Ser Phe
 65                  70                  75                  80

Thr Thr Asn Val Val Ala Ala Pro Val Leu Tyr Cys Lys Arg Thr
             85                  90                  95

Leu Asp Ile Ser Asn Thr Ala Arg Ala Val Leu Thr Asn Ala Gly Gln
                100                 105                 110

Ala Asn Ala Ala Thr Gly Lys Glu Gly Tyr Gln Asp Met Ile Glu Cys
            115                 120                 125

Val Glu Ser Leu Ala Lys Leu Leu Lys Val Lys Pro Glu Glu Val Leu
    130                 135                 140

Ile Glu Ser Thr Gly Val Ile Gly Gln Arg Ile Lys Lys Gly Ala Leu
145                 150                 155                 160

Leu Asn Ser Leu Pro Thr Leu Val Asn Ser Leu Ser Ser Ser Val Glu
                165                 170                 175

Gly Ala Asp Ser Ala Ala Val Ala Ile Thr Thr Thr Asp Leu Val Ser
            180                 185                 190

Lys Ser Val Ala Ile Glu Ser Leu Ile Gly Gly Thr Lys Val Arg Val
    195                 200                 205

Gly Gly Met Ala Lys Gly Ser Gly Met Ile His Pro Asn Met Ala Thr
210                 215                 220

Met Leu Gly Val Ile Thr Thr Asp Ala Arg Leu Thr Ser Asp Val Trp
225                 230                 235                 240

Arg Lys Met Val Gln Val Ala Val Asn Arg Ser Phe Asn Gln Ile Thr
                245                 250                 255

Val Asp Gly Asp Thr Ser Thr Asn Asp Thr Val Ile Ala Leu Ala Ser
            260                 265                 270

Gly Leu Ser Gly Leu Gly Cys Ile Ser Ser Leu Asp Ser Asp Glu Ala
    275                 280                 285

Ile Gln Leu Gln Ala Cys Leu Asp Ala Val Met Gln Gly Leu Ala Lys
290                 295                 300

Ser Ile Ala Trp Asp Gly Glu Gly Ala Thr Cys Leu Val Glu Val Cys
305                 310                 315                 320

Val Thr Gly Ala Asn Ser Glu Ala Glu Ala Lys Val Ala Arg Ser
                325                 330                 335

Val Ala Ser Ser Ser Leu Val Lys Ala Ala Ile Tyr Gly Arg Asp Pro
            340                 345                 350

Asn Trp Gly Arg Ile Ala Ala Ala Gly Tyr Ser Gly Val Ser Phe
    355                 360                 365

His Gln Asp Leu Leu Arg Val Glu Leu Gly Asp Ile Leu Leu Met Asp
370                 375                 380

Gly Gly Glu Pro Gln Leu Phe Asp Arg His Ala Ala Ser Ser Tyr Leu
385                 390                 395                 400

Arg Lys Ala Gly Glu Thr His Asp Thr Val Lys Ile Gln Ile Ser Val
                405                 410                 415

Gly Asn Gly Pro Gly Arg Gly Gln Ala Trp Gly Cys Asp Leu Ser Tyr
            420                 425                 430

Asp Tyr Val Lys Ile Asn Ala Glu Tyr Thr Thr
        435                 440
```

<210> SEQ ID NO: 15
<211> LENGTH: 723
<212> TYPE: DNA
<213> ORGANISM: Nicotiana plumbaginifolia
<220> FEATURE:

-continued

```
<221> NAME/KEY: unsure
<222> LOCATION: (2)
<220> FEATURE:
<221> NAME/KEY: unsure
<222> LOCATION: (28)
<220> FEATURE:
<221> NAME/KEY: unsure
<222> LOCATION: (138)
<220> FEATURE:
<221> NAME/KEY: unsure
<222> LOCATION: (178)
<220> FEATURE:
<221> NAME/KEY: unsure
<222> LOCATION: (317)
<220> FEATURE:
<221> NAME/KEY: unsure
<222> LOCATION: (339)
<220> FEATURE:
<221> NAME/KEY: unsure
<222> LOCATION: (353)
<220> FEATURE:
<221> NAME/KEY: unsure
<222> LOCATION: (415)
<220> FEATURE:
<221> NAME/KEY: unsure
<222> LOCATION: (426)
<220> FEATURE:
<221> NAME/KEY: unsure
<222> LOCATION: (461)
<220> FEATURE:
<221> NAME/KEY: unsure
<222> LOCATION: (502)
<220> FEATURE:
<221> NAME/KEY: unsure
<222> LOCATION: (532)
<220> FEATURE:
<221> NAME/KEY: unsure
<222> LOCATION: (534)
<220> FEATURE:
<221> NAME/KEY: unsure
<222> LOCATION: (547)
<220> FEATURE:
<221> NAME/KEY: unsure
<222> LOCATION: (556)
<220> FEATURE:
<221> NAME/KEY: unsure
<222> LOCATION: (565)
<220> FEATURE:
<221> NAME/KEY: unsure
<222> LOCATION: (570)
<220> FEATURE:
<221> NAME/KEY: unsure
<222> LOCATION: (592)
<220> FEATURE:
<221> NAME/KEY: unsure
<222> LOCATION: (616)
<220> FEATURE:
<221> NAME/KEY: unsure
<222> LOCATION: (637)
<220> FEATURE:
<221> NAME/KEY: unsure
<222> LOCATION: (654)
<220> FEATURE:
<221> NAME/KEY: unsure
<222> LOCATION: (660)..(661)
<220> FEATURE:
<221> NAME/KEY: unsure
<222> LOCATION: (665)..(666)
<220> FEATURE:
<221> NAME/KEY: unsure
<222> LOCATION: (677)
<220> FEATURE:
<221> NAME/KEY: unsure
<222> LOCATION: (684)
<220> FEATURE:
<221> NAME/KEY: unsure
<222> LOCATION: (686)
<220> FEATURE:
<221> NAME/KEY: unsure
```

<222> LOCATION: (688)
<220> FEATURE:
<221> NAME/KEY: unsure
<222> LOCATION: (693)
<220> FEATURE:
<221> NAME/KEY: unsure
<222> LOCATION: (700)
<220> FEATURE:
<221> NAME/KEY: unsure
<222> LOCATION: (713)
<220> FEATURE:
<221> NAME/KEY: unsure
<222> LOCATION: (715)

<400> SEQUENCE: 15

```
gncacgagat tacatagcct ctcccaanca atgtctttat ctgttcctca tttcatctct     60
gtccaattct ccaacctcaa tggattaaag gtgcaggcat atgggtgcc aaagcaatta    120
aggagagatt ttaaagtntt agcagttaca tcaatgtcaa aggaagcatc aaattatnta    180
ccagcagctc ctattttcct acctgaagga ccatggcagc agattcctgg tggtgttact    240
gctgcaaagg gtttcaaagc tgctgggatg tatggtggat tgcgtgctct tggagagaag    300
cctgatctcg cactcgncac ttgtgatgta gatgccatnt ctgcagggc atntactaca     360
aatgttgttg cagctgcacc tgtactatac tgtaaaagcg cactacatgc atctnaaacg    420
ggtcgngcgg tattaataaa tgctggtcaa gctaatgcga naccgggtga tgcaggttat    480
caggatgtta tagagtgctc tngtgcactg gctcagttac ttcaactgaa gnangatgaa    540
gtcttgntcg actccnctgg gggtntaggn caaagaataa aggaggggg anttctcaac    600
tcaatcccca cctggntagg cagcttccac aactttnggg ggggaagttc tctncagttn    660
ntttnncccc cctttctgc ttcncnantc ggnttttgtn cagggctcaa ggnaccccct    720
tca                                                                  723
```

<210> SEQ ID NO: 16
<211> LENGTH: 198
<212> TYPE: PRT
<213> ORGANISM: Nicotiana plumbaginifolia
<220> FEATURE:
<221> NAME/KEY: UNSURE
<222> LOCATION: (50)
<220> FEATURE:
<221> NAME/KEY: UNSURE
<222> LOCATION: (96)
<220> FEATURE:
<221> NAME/KEY: UNSURE
<222> LOCATION: (103)
<220> FEATURE:
<221> NAME/KEY: UNSURE
<222> LOCATION: (108)
<220> FEATURE:
<221> NAME/KEY: UNSURE
<222> LOCATION: (129)
<220> FEATURE:
<221> NAME/KEY: UNSURE
<222> LOCATION: (144)
<220> FEATURE:
<221> NAME/KEY: UNSURE
<222> LOCATION: (158)
<220> FEATURE:
<221> NAME/KEY: UNSURE
<222> LOCATION: (168)
<220> FEATURE:
<221> NAME/KEY: UNSURE
<222> LOCATION: (173)
<220> FEATURE:
<221> NAME/KEY: UNSURE
<222> LOCATION: (176)
<220> FEATURE:
<221> NAME/KEY: UNSURE

```
<222> LOCATION: (179)
<220> FEATURE:
<221> NAME/KEY: UNSURE
<222> LOCATION: (188)
<220> FEATURE:
<221> NAME/KEY: UNSURE
<222> LOCATION: (196)

<400> SEQUENCE: 16

Met Ser Leu Ser Val Pro His Phe Ile Ser Val Gln Phe Ser Asn Leu
 1               5                  10                  15

Asn Gly Leu Lys Val Gln Ala Tyr Gly Val Pro Lys Gln Leu Arg Arg
            20                  25                  30

Asp Phe Lys Val Leu Ala Val Thr Ser Met Ser Lys Glu Ala Ser Asn
        35                  40                  45

Tyr Xaa Pro Ala Ala Pro Ile Phe Leu Pro Glu Gly Pro Trp Gln Gln
    50                  55                  60

Ile Pro Gly Gly Val Thr Ala Ala Lys Gly Phe Lys Ala Ala Gly Met
 65                  70                  75                  80

Tyr Gly Gly Leu Arg Ala Leu Gly Glu Lys Pro Asp Leu Ala Leu Xaa
                85                  90                  95

Thr Cys Asp Val Asp Ala Xaa Ser Ala Gly Ala Xaa Thr Thr Asn Val
                100                 105                 110

Val Ala Ala Ala Pro Val Leu Tyr Cys Lys Ser Ala Leu His Ala Ser
            115                 120                 125

Xaa Thr Gly Arg Ala Val Leu Ile Asn Ala Gly Gln Ala Asn Ala Xaa
130                 135                 140

Pro Gly Asp Ala Gly Tyr Gln Asp Val Ile Glu Cys Ser Xaa Ala Leu
145                 150                 155                 160

Ala Gln Leu Leu Gln Leu Lys Xaa Asp Glu Val Leu Xaa Asp Ser Xaa
                165                 170                 175

Gly Gly Xaa Gly Gln Arg Ile Lys Glu Gly Gly Xaa Leu Asn Ser Ile
            180                 185                 190

Pro Thr Trp Xaa Gly Ser
            195

<210> SEQ ID NO: 17
<211> LENGTH: 620
<212> TYPE: DNA
<213> ORGANISM: Triticum aestivum
<220> FEATURE:
<221> NAME/KEY: unsure
<222> LOCATION: (229)
<220> FEATURE:
<221> NAME/KEY: unsure
<222> LOCATION: (234)
<220> FEATURE:
<221> NAME/KEY: unsure
<222> LOCATION: (314)
<220> FEATURE:
<221> NAME/KEY: unsure
<222> LOCATION: (363)
<220> FEATURE:
<221> NAME/KEY: unsure
<222> LOCATION: (411)
<220> FEATURE:
<221> NAME/KEY: unsure
<222> LOCATION: (424)
<220> FEATURE:
<221> NAME/KEY: unsure
<222> LOCATION: (429)
<220> FEATURE:
<221> NAME/KEY: unsure
<222> LOCATION: (435)
<220> FEATURE:
```

-continued

```
<221> NAME/KEY: unsure
<222> LOCATION: (445)
<220> FEATURE:
<221> NAME/KEY: unsure
<222> LOCATION: (450)
<220> FEATURE:
<221> NAME/KEY: unsure
<222> LOCATION: (452)
<220> FEATURE:
<221> NAME/KEY: unsure
<222> LOCATION: (456)
<220> FEATURE:
<221> NAME/KEY: unsure
<222> LOCATION: (467)..(468)..(469)
<220> FEATURE:
<221> NAME/KEY: unsure
<222> LOCATION: (480)
<220> FEATURE:
<221> NAME/KEY: unsure
<222> LOCATION: (506)
<220> FEATURE:
<221> NAME/KEY: unsure
<222> LOCATION: (525)..(526)
<220> FEATURE:
<221> NAME/KEY: unsure
<222> LOCATION: (552)
<220> FEATURE:
<221> NAME/KEY: unsure
<222> LOCATION: (554)
<220> FEATURE:
<221> NAME/KEY: unsure
<222> LOCATION: (566)
<220> FEATURE:
<221> NAME/KEY: unsure
<222> LOCATION: (570)
<220> FEATURE:
<221> NAME/KEY: unsure
<222> LOCATION: (575)
<220> FEATURE:
<221> NAME/KEY: unsure
<222> LOCATION: (581)
<220> FEATURE:
<221> NAME/KEY: unsure
<222> LOCATION: (597)
<220> FEATURE:
<221> NAME/KEY: unsure
<222> LOCATION: (604)
<220> FEATURE:
<221> NAME/KEY: unsure
<222> LOCATION: (607)

<400> SEQUENCE: 17
ctacggcggc ctgcgcgcca agggacagaa gcctgacttg gcgcttgttg cttgcgacgt      60
cgacgccacc gtcgccggat cttttacaac aaatgttgtt gctgctgcgc ctgttctgta     120
ttgcaagcgt gtccttagtt catccaaaac agctcgtgct gtgttgatta atgctggtca     180
agcaaatgca gccactggtg atgcaggata tcaggacgca cgtggatant gcanaagctg     240
ttgccaagct tttgaatgtg agcacaaatg acatactgat ccagtccact ggtgtcattg     300
gtcaaaagaa taanaaagga agcacttata aattcacttc ctagacttgt gggctctctg     360
tcntcatcta ctgaaggtca aattcttcag ctgtggccat acaactaca nacctgttac      420 caanataant gctgncaaca cgaanattgn angatnccat caacgannng acgaaggcan     480
aggtctggga tgatcatcca atatgngaaa agcctggtgt tccannaccg atctaattag     540
aatgatgttg gnanaaaggc cggcanattn taaantcacc naatacgtgg tgtgaanata     600
gatnagngta tgcatgcaag                                                 620

<210> SEQ ID NO: 18
<211> LENGTH: 393
<212> TYPE: PRT
```

<213> ORGANISM: Triticum aestivum

<400> SEQUENCE: 18

```
Thr Ser Tyr Gly Gly Leu Arg Ala Lys Gly Gln Lys Pro Asp Leu Ala
  1               5                  10                  15

Leu Val Ala Cys Asp Val Asp Ala Thr Val Ala Gly Ser Phe Thr Thr
                 20                  25                  30

Asn Val Ala Ala Ala Pro Val Leu Tyr Cys Lys Arg Val Leu Ser
             35                  40                  45

Ser Ser Lys Thr Ala Arg Ala Val Leu Ile Asn Ala Gly Gln Ala Asn
         50                  55                  60

Ala Ala Thr Gly Asp Ala Gly Tyr Gln Asp Ala Val Asp Ser Ala Glu
 65                  70                  75                  80

Ala Val Ala Lys Leu Leu Asn Val Ser Thr Asn Asp Ile Leu Ile Gln
                 85                  90                  95

Ser Thr Gly Val Ile Gly Gln Arg Ile Lys Lys Glu Ala Leu Ile Asn
             100                 105                 110

Ser Leu Pro Arg Leu Val Gly Ser Leu Ser Ser Thr Glu Gly Ser
         115                 120                 125

Asn Ser Ser Ala Val Ala Ile Thr Thr Thr Asp Leu Val Ser Lys Ser
130                 135                 140

Ile Ala Val Gln Thr Glu Ile Gly Gly Val Pro Ile Lys Ile Gly Gly
145                 150                 155                 160

Met Ala Lys Gly Ser Gly Met Ile His Pro Asn Met Ala Thr Met Leu
                 165                 170                 175

Gly Val Leu Thr Thr Asp Ala Gln Val Arg Ser Asp Val Trp Arg Glu
             180                 185                 190

Met Val Arg Thr Ser Val Ser Arg Ser Phe Asn Gln Ile Thr Val Asp
         195                 200                 205

Gly Asp Thr Ser Thr Asn Asp Cys Val Ile Ala Met Ala Ser Gly Leu
210                 215                 220

Ser Gly Leu Ser Asp Ile Leu Thr His Asp Ser Ala Glu Ala Gln Gln
225                 230                 235                 240

Leu Gln Ala Cys Leu Asp Ala Val Met Gln Gly Leu Ala Lys Ser Ile
                 245                 250                 255

Ala Trp Asp Gly Glu Gly Ala Thr Cys Leu Ile Glu Val Thr Val Thr
             260                 265                 270

Gly Ala Asn Asn Glu Ala Asp Ala Ala Lys Ile Ala Arg Ser Val Ala
         275                 280                 285

Ala Ser Ser Leu Val Lys Ala Val Phe Gly Arg Asp Pro Asn Trp
290                 295                 300

Gly Arg Ile Ala Cys Ser Val Gly Tyr Ser Gly Ile His Phe Asp Ala
305                 310                 315                 320

Asp Gln Leu Asp Ile Ser Leu Gly Val Ile Pro Leu Met Lys Asn Gly
                 325                 330                 335

Gln Pro Leu Pro Phe Asp Arg Ser Ala Ala Ser Lys Tyr Leu Lys Asp
             340                 345                 350

Ala Gly Asp Ile His Gly Thr Val Asn Ile Asp Val Ser Val Gly Asn
         355                 360                 365

Gly Gly Gly Thr Gly Lys Ala Trp Gly Cys Asp Leu Ser Tyr Lys Tyr
370                 375                 380

Val Glu Ile Asn Ala Glu Tyr Thr Thr
385                 390
```

# ORNITHINE BIOSYNTHESIS ENZYMES

This application claims the benefit of U.S. Provisional Application No. 60/093,209, filed Jul. 17, 1998.

FIELD OF THE INVENTION

This invention is in the field of plant molecular biology. More specifically, this invention pertains to nucleic acid fragments encoding ornithine biosynthetic enzymes in plants and seeds.

BACKGROUND OF THE INVENTION

Ornithine is converted into arginine in the urea cycle. Intermediaries in the ornithine biosynthesis pathway are important in other steps of this cycle. Amino acid N-acetyl transferase (EC 2.3.1.1) catalyzes the first reaction in a pathway that leads to the synthesis of ornithine from L-glutamate giving N-acetylglutamate as its intermediary product.

Carbamoyl phosphate synthase I, the mitochondrial enzyme that catalyzes the first committed step of the urea cycle, is allosterically activated by N-acetyl glutamate. The rate of urea production by the liver is, in fact, correlated with the N-acetylglutamate concentration. Increased urea synthesis is required when amino acid breakdown rates increase, generating excess nitrogen that must be extracted. Increase in these breakdown rates are signaled by an increase in glutamate concentration through transamination reaction. This situation, in turn, causes an increase in N-acetylglutamate synthesis, stimulating carbamoyl phosphate synthetase and the entire urea cycle.

N-acetylglutamate kinase (EC 2.7.2.8) catalyzes the conversion of N-acetyl-L-glutamate and ATP into N-acetyl-L-glutamate-5-phosphate and ADP. N-acetyl-gamnma-glutamyl-phosphate reductase (EC 1.2.1.38) catalyzes the convertion of N-acetyl-L-glutamate 5-phosphate and NADPH to orthophosphate, NADP and N-acetyl-L-glutamate-5-semialdehyde. This activity is encoded by the argC locus in bacteria and *Synechocystis*. To date this gene has not been described in plants.

N-2-Acetyl-L-ornithine and L-glutamate are converted to ornithine in the presence of glutamate N-acetyl transferase (EC 2.3.1.35), also called ornithine acetyltransferase. This enzyme is encoded by the argJ locus in bacteria and *Synechocystis*. This enzyme is active in the mitochondrial matrix as a heterodimer consisting of two subunits processed from the same precursor protein.

SUMMARY OF THE INVENTION

The instant invention relates to isolated nucleic acid fragments encoding ornithine biosynthetic enzymes. Specifically, this invention concerns an isolated nucleic acid fragment encoding a N-acetyl-gamma-glutamyl phosphate reductase or a glutamate N-acetyl transferase and an isolated nucleic acid fragment that is substantially similar to an isolated nucleic acid fragment encoding a N-acetyl-gamma-glutamyl phosphate reductase or a glutamate N-acetyl transferase. In addition, this invention relates to a nucleic acid fragment that is complementary to the nucleic acid fragment encoding N-acetyl-gamma-glutamyl phosphate reductase or glutamate N-acetyl transferase.

An additional embodiment of the instant invention pertains to a polypeptide encoding all or a substantial portion of an ornithine biosynthetic enzyme selected from the group consisting of N-acetyl-gamma-glutamyl phosphate reductase and glutamate N-acetyl transferase.

In another embodiment, the instant invention relates to a chimeric gene encoding a N-acetyl-gamma-glutamyl phosphate reductase or a glutamate N-acetyl transferase, or to a chimeric gene that comprises a nucleic acid fragment that is complementary to a nucleic acid fragment encoding a N-acetyl-gamma-glutamyl phosphate reductase or a glutamate N-acetyl transferase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a N-acetyl-gamma-glutamyl phosphate reductase or a glutamate N-acetyl transferase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a N-acetyl-gamma-glutamyl phosphate reductase or a glutamate N-acetyl transferase in a transformed host cell comprising: a) transforming a host cell with a chimeric gene comprising a nucleic acid fragment encoding a N-acetyl-gamma-glutamyl phosphate reductase or a glutamate N-acetyl transferase; and b) growing the transformed host cell under conditions that are suitable for expression of the chimeric gene wherein expression of the chimeric gene results in production of altered levels of N-acetyl-gamma-glutamyl phosphate reductase or glutamate N-acetyl transferase in the transformed host cell.

An addition embodiment of the instant invention concerns a method for obtaining a nucleic acid fragment encoding all or a substantial portion of an amino acid sequence encoding a N-acetyl-gamma-glutamyl phosphate reductase or a glutamate N-acetyl transferase.

A further embodiment of the instant invention is a method for evaluating at least one compound for its ability to inhibit the activity of a N-acetyl-gamma-glutamyl phosphate reductase or a glutamate N-acetyl transferase, the method comprising the steps of: (a) transforming a host cell with a chimeric gene comprising a nucleic acid fragment encoding a N-acetyl-gamma-glutamyl phosphate reductase or a glutamate N-acetyl transferase, operably linked to suitable regulatory sequences; (b) growing the transformed host cell under conditions that are suitable for expression of the chimeric gene wherein expression of the chimeric gene results in production of N-acetyl-gamma-glutamyl phosphate reductase or glutamate N-acetyl transferase in the transformed host cell; (c) optionally purifying the N-acetyl-gamma-glutamyl phosphate reductase or the glutamate N-acetyl transferase expressed by the transformed host cell; (d) treating the N-acetyl-gamma-glutamyl phosphate reductase or the glutamate N-acetyl transferase with a compound to be tested; and (e) comparing the activity of the N-acetyl-gamma-glutamyl phosphate reductase or the glutamate N-acetyl transferase that has been treated with a test compound to the activity of an untreated N-acetyl-gamma-glutamyl phosphate reductase or glutamate N-acetyl transferase, thereby selecting compounds with potential for inhibitory activity.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Ornithine Biosynthetic Enzymes

| | | SEQ ID NO: | |
|---|---|---|---|
| Protein | Clone Designation | (Nucleotide) | (Amino Acid) |
| Jerusalem artichoke N-acetyl-gamma-glutamyl phosphate reductase | hel1.pk0002.h8 | 1 | 2 |
| Corn N-acetyl-gamma-glutamyl phosphate reductase | Contig of: cco1.pk0046.h7 ceb1.pk0026.g8 cr1n.pk0185.a9 p0003.cgpfk13r p0044.cjraf16r p0128.cpiar56r | 3 | 4 |
| Rice N-acetyl-gamma-glutamyl phosphate reductase | rr1n.pk001.h10 | 5 | 6 |
| Soybean N-acetyl-gamma-glutamyl phosphate reductase | ses4d.pk0004.e10 | 7 | 8 |
| Wheat N-acetyl-gamma-glutamyl phosphate reductase | wlm96.pk037.f18 | 9 | 10 |
| Corn glutamate N-acetyl transferase | Contig of: p0004.cb1ec29r p0016.ctsav50r p0032.crcag34r p0080.cgaba55r | 11 | 12 |
| Soybean glutamate N-acetyl transferase | sdp4c.pk038.d4 | 13 | 14 |
| Tobacco glutamate N-acetyl transferase | np.02a10.sk20 | 15 | 16 |
| Wheat glutamate N-acetyl transferase | wlmk1.pk0015.a2 | 17 | 18 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5%

SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several ornithine biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other ornithine biosynthetic enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36: 1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of arginine in those cells. Extra arginine resulting from an increase in ornithine biosynthesis may have nutraceutical utility.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded orithine biosynthetic enzyme. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in arginine biosynthesis. Accordingly, inhibition of the activity of one or both of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad.*

Sci USA 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, Jerusalem artichoke, rice, soybean, tobacco and wheat tissues were prepared. The characteristics of the libraries are described below.

TABLE 2 cDNA Libraries from Corn, Jerusalem Artichoke, Rice, Soybean, Tobacco and Wheat

| Library | Tissue | Clone |
|---|---|---|
| cco1 | Corn Cob of 67 Day Old Plants Grown in Green House | cco1.pk0046.h7 |
| ceb1 | Corn Embryo 10 to 11 Days After Pollination | ceb1.pk0026.g8 |
| cr1n | Corn Root From 7 Day Old Seedlings* | cr1n.pk0185.a9 |
| he11 | Jerusalem Artichoke Tuber | he11.pk0002.h8 |
| np | *Nicotiana plumb* Leaf | np.02a10.sk20 |
| p0003 | Corn Premeiotic Ear Shoot, 0.2–4 cm | p0003.cgpfk13r |
| p0004 | Corn Immature Ear | p0004.cb1ec29r |
| p0016 | Corn Tassel Shoots, 0.1–1.4 cm, Pooled | p0016.ctsav50r |
| p0032 | Corn Regenerating Callus (Hi-II 223a and 1129e), 10 and 14 Days After Auxin Removal | p0032.crcag34r |
| p0044 | Corn Pedicel 20 Days After Pollination | p0044.cjraf16r |
| p0080 | Corn Vegetative Meristems from V3** Stage Seedlings | p0080.cgaba55r |
| p0128 | Corn Primary and Secondary Immature Ear | p0128.cpiar56r |
| rr1n | Rice Root of Two Week Old Developing Seedling* | rr1n.pk001.h10 |
| sdp4c | Soybean Developing Pods (10–12 mm) | sdp4c.pk038.d4 |

TABLE 2-continued cDNA Libraries from Corn, Jerusalem Artichoke, Rice, Soybean, Tobacco and Wheat

| Library | Tissue | Clone |
|---|---|---|
| ses4d | Soybean Embryogenic Suspension 4 Days After Subculture | ses4d.pk0004.e10 |
| wlm96 | Wheat Seedlings 96 Hours After Inoculation With *Erysiphe graminis f. sp tritici* | wlm96.pk037.f18 |
| wlmk1 | Wheat Seedlings 1 Hour After Inoculation With *Erysiphe graminis f. sp tritici* and Treatment With Herbicide*** | wlmk1.pk0015.a2 |

*This library was normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding ornithine biosynthetic enzymes were identified by conducting BLAST (Basic Local Alignment Search Tool; Altschul et al. (1993) *J Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3
Characterization of cDNA Clones Encoding N-Acetyl-Gamma-Glutamyl Phosphate Reductase The BLASTX search using the EST sequences from clones listed in Table 3 revealed similarity of the polypeptides encoded by the cDNAs to N-acetyl-gamma-glutamyl phosphate reductase from *Arabidopsis thaliana* (NCBI General Identifier No. 3687224). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to N-Acetyl-Gamma-Glutamyl Phosphate Reductase

| Clone | Status | BLAST pLog Score 3687224 |
|---|---|---|
| hel1.pk0002.h8 | FIS | 126.00 |
| Contig of: | Contig | 134.00 |
| cco1.pk0046.h7 | | |
| ceb1.pk0026.g8 | | |
| cr1n.pk0185.a9 | | |
| p0003.cgpfk13r | | |
| p0044.cjraf16r | | |
| p0128.cpiar56r | | |
| rr1n.pk001.h10 | EST | 21.00 |
| ses4d.pk0004.e10 | FIS | 140.00 |
| wlm96.pk037.f18 | FIS | 135.00 |

The data in Table 4 represents a calculation of the percent identity of the amino acid 10 sequences set forth in SEQ ID NOs:2, 4, 6, 8 and 10 and the *Arabidopsis thaliana* sequence (NCBI General Identifier No. 3687224).

TABLE 4

Percent Identity of Amino Acid Sequences Deduced From the Nucleotide Sequences of cDNA Clones Encoding Polypeptides Homologous to N-Acetyl-Gamma-Glutamyl Phosphate Reductase

| SEQ ID NO. | Percent Identity to 3687224 |
|---|---|
| 2 | 66.6 |
| 4 | 61.4 |
| 6 | 38.5 |
| 8 | 61.7 |
| 10 | 61.7 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a portion of a rice N-acetyl-gamma-glutamyl phosphate reductase, a substantial portion of a Jerusalem artichoke N-acetyl-gamma-glutamyl phosphate reductase and entire corn, soybean and wheat N-acetyl-gamma-glutamyl phosphate reductase. These sequences represent the first Jerusalem artichoke, corn, rice, soybean and wheat sequences encoding N-acetyl-gamma-glutamyl phosphate reductase.

Example 4
Characterization of cDNA Clones Encoding Glutamate N-Acetyl Transferase The BLASTX search using the EST sequences from clones listed in Table 3 revealed similarity of the polypeptides encoded by the cDNAs to glutamate N-acetyl transferase from *Arabidopsis thaliana* (NCBI General Identifier No. 4056500). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to Glutamate N-Acetyl Transferase

| Clone | Status | BLAST pLog Score 4056500 |
|---|---|---|
| Contig of: | Contig | 118.00 |
| p0004.cb1ec29r | | |
| p0016.ctsav50r | | |
| p0032.crcag34r | | |
| p0080.cgaba55r | | |
| sdp4c.pk038.d4 | FIS | 161.00 |
| np.02a10.sk20 | EST | 41.70 |
| wlmk1.pk0015.a2 | FIS | 150.0 |

The data in Table 6 represents a calculation of the percent identity of the amino acid sequences set forth in SEQ ID NOs: 12, 14, 16 and 18 and the *Arabidopsis thaliana* sequence (NCBI General Identifier No. 4056500).

TABLE 6

Percent Identity of Amino Acid Sequences Deduced From the Nucleotide Sequences of cDNA Clones Encoding Polypeptides Homologous to Glutamate N-Acetyl Transferase

| SEQ ID NO. | Percent Identity to 4056500 |
|---|---|
| 12 | 58.4 |
| 14 | 67.1 |
| 16 | 37.5 |
| 18 | 67.0 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a tobacco and a wheat glutamate N-acetyl transferases and entire corn and soybean glutamate N-acetyl transferases.

These sequences represent the first corn, soybean, tobacco and wheat sequences encoding glutamate N-acetyl transferase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of 30 $\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the $\beta$ subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve OTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL2 1 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8
Evaluating Compounds for Their Ability to Inhibit the Activity of Ornithine Biosynthetic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for N-acetyl-gamma-glutamyl phosphate reductase and glutamate N-acetyl transferase are presented by Cybis, J. and Davis, R. H. (1975) *J. Bacteriol.* 123:196–202.

What is claimed is:

1. An isolated nucleic acid fragment comprising a member selected from the group consisting of:
   (a) an isolated nucleic acid fragment encoding an N-acetyl-gamma-glutamyl phosphate reductase having an amino acid sequence that is at least 80% identical to the amino acid sequence set forth in a member selected from the group consisting of SEQ ID NOs: 2, 4, 6, 8, and 10; and
   (b) an isolate nucleic acid fragment that is complementary to (a).

2. The isolated nucleic acid fragment of claim 1 wherein the nucleic acid fragment is a functional RNA.

3. The isolated nucleic acid fragment of claim 1 wherein the nucleotide sequence of the fragment comprises the sequence set forth in a member selected from the group consisting of SEQ ID NO:1, SEQ ID NO:3, SEQ ID NO:5, SEQ ID NO:7 and SEQ ID NO:9.

4. A chimeric gene comprising the nucleic acid fragment of claim 1 operably linked to suitable regulatory sequences.

5. A transformed host cell comprising the chimeric gene of claim 4.

* * * * *